United States Patent
Lorraine et al.

(10) Patent No.: US 10,555,679 B2
(45) Date of Patent: Feb. 11, 2020

(54) NON-CONTACT HEART RATE MONITORING

(71) Applicant: GENERAL ELECTRIC COMPANY, Schenectady, NY (US)

(72) Inventors: Peter Lorraine, Niskayuna, NY (US); David Davenport, Niskayuna, NY (US); Tzu-Jen Kao, Niskayuna, NY (US); Aghogho Obi, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/627,509

(22) Filed: Jun. 20, 2017

(65) Prior Publication Data

US 2018/0360324 A1    Dec. 20, 2018

(51) Int. Cl.
*A61B 5/00* (2006.01)
*A61B 5/024* (2006.01)
*G06K 9/20* (2006.01)
*G06K 9/00* (2006.01)

(52) U.S. Cl.
CPC ............ *A61B 5/024* (2013.01); *A61B 5/0002* (2013.01); *G06K 9/2018* (2013.01); *G06K 2009/00939* (2013.01)

(58) Field of Classification Search
CPC .......... A61B 5/68–6812; A61B 5/6844; A61B 5/024; A61B 5/0205; A61B 5/02411; A61B 5/7275; A61B 5/6892; A61B 5/0002; A61B 2562/0214; A61B 2503/045; A61B 2562/046; G06K 9/2018; G06K 2009/00939
See application file for complete search history.

(56) References Cited

U.S. PATENT DOCUMENTS

| | | | |
|---|---|---|---|
| 7,689,271 B1 | 3/2010 | Sullivan | |
| 7,740,588 B1 | 6/2010 | Sciarra | |
| 8,430,817 B1 * | 4/2013 | Al-Ali | A61B 5/7221 600/301 |
| 9,504,616 B2 | 11/2016 | Belsinger, Jr. et al. | |
| 2006/0015027 A1 | 1/2006 | Matthews et al. | |

(Continued)

FOREIGN PATENT DOCUMENTS

KR    20120102201 A    9/2012

OTHER PUBLICATIONS

"Babysense" Hisense Health Monitoring Technologies, 2015.

(Continued)

*Primary Examiner* — Scott M. Getzow

(74) *Attorney, Agent, or Firm* — McCoy Russell LLP

(57) ABSTRACT

There is set forth herein an apparatus comprising: a non-contacting array of sensors adapted for positioning at a position spaced from and proximate a position of a patient; and a signal processing circuit in communication with the array of sensors, wherein the signal processing circuit is configured for: generating a plurality of time varying signals using the array of sensors; processing the plurality of time varying signals; and outputting one or more indicator based on the processing. The apparatus can be adapted for use in a variety of applications including emergency applications such as live birth applications in which neonate resuscitation protocols are observed.

32 Claims, 7 Drawing Sheets

(56) References Cited

U.S. PATENT DOCUMENTS

| | | |
|---|---|---|
| 2007/0149883 A1 | 6/2007 | Yesha |
| 2010/0191136 A1 | 7/2010 | Wolford |
| 2012/0265080 A1* | 10/2012 | Yu .............................. A61B 5/04 |
| | | 600/484 |
| 2012/0299732 A1 | 11/2012 | Vogel |
| 2013/0116578 A1* | 5/2013 | An ....................... A61B 5/0205 |
| | | 600/484 |
| 2015/0119656 A1* | 4/2015 | Foster ................... A61B 5/6892 |
| | | 600/301 |
| 2015/0196257 A1* | 7/2015 | Yousefi .................. A61B 5/024 |
| | | 600/324 |
| 2016/0374566 A1 | 12/2016 | Fung et al. |
| 2017/0156608 A1 | 6/2017 | Mahar |

OTHER PUBLICATIONS

Ferreira, et al. "A Smart Wearable System for Sudden Infant Death Syndrome Monitoring," IEEE International Conference Industrial Technology (ICIT), Mar. 14, 2016.

Mora, et al. Evaluation of Pressure Bed Sensor for Automatic Sahs Screening,: IEEE Transactions on Instrumentation and Measurement, pp. 1935-1943, vol. 64, Issue 7, Jul. 2015.

Isa Korean Intellectual Property Office, International Search Report and Written Opinion Issued in Application No. PCT/US2018/033424, dated Dec. 11, 2018, WIPO, 15 pages.

\* cited by examiner

NON-CONTACT HEART RATE MONITORING

BACKGROUND

Patient monitoring systems include electronic monitoring devices designed to display physiological information about a patient. Electrocardiogram (ECG), electroencephalogram (EEG), plethysmographic signals, and signals related to blood pressure, temperature, and respiration represent typical physiological information contained in monitoring devices. Patient monitoring systems are typically also furnished with alarming functionality to alert clinicians of important physiological events that may impact a patient being monitored. Such systems maintain alarm configuration settings that are used to determine when an alarm event is triggered by the devices.

Electric fields can be developed in free space from many different sources. For Organs in the human body such as the heart and brain produce electric fields. Electrocardiogram (ECG) provide a measurement of electric fields produced by the heart. Current methods of measuring electric potentials associated with a human employ securing electrodes directly to the skin of a patient. Methods requiring direct contact with the skin of a patent have been observed to yield patient discomfort. Time for signal generation can be significant and includes setup time to secure electrodes to the skin of a patient.

Fast acquisition of heart rate readings can be especially important in a variety of applications including in the delivery of babies. Current clinical practice includes internationally accepted protocol for neonatal resuscitation. This protocol uses heart rate of a newly born neonate to decide whether breathing assistance is applied to the neonate and what types of breathing interventions are to be used. Current clinical practice involves a nurse holding the umbilical cord to count blood pulses or else using a stethoscope to hear the neonate's heart beats. Both of these methods are proven to be erroneous (published in literature). In addition, these methods are performed only at fixed intervals (i.e. at 30 seconds, at 60 seconds) rather than continuously. Finally, sharing the estimated heart beat with other caregivers in the labor & delivery room is challenging leading to miscommunication and possibility of erroneous decisions. Recent version 7 of the Neonatal Resuscitation Protocol recommends the use of ECG monitoring to improve accuracy. However, such a device requires adhesive electrodes applied to the neonate with cables connecting the neonate to the cardiac monitor. Electrodes are difficult to place on newborn skin due to fluids and removing or repositioning sensors can damage the fragile skin. Cables get in the way when nurses are cleaning the neonate and applying ventilation therapy.

BRIEF DESCRIPTION

There is set forth herein an apparatus comprising: a non-contacting array of sensors adapted for positioning at a position spaced from and proximate a position of a patient; and a signal processing circuit in communication with the array of sensors, wherein the signal processing circuit is configured for: generating a plurality of time varying signals using the array of sensors; processing the plurality of time varying signals; and outputting one or more indicator based on the processing. The apparatus can be adapted for use in a variety of applications including emergency applications such as live birth applications in which neonate resuscitation protocols are observed.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
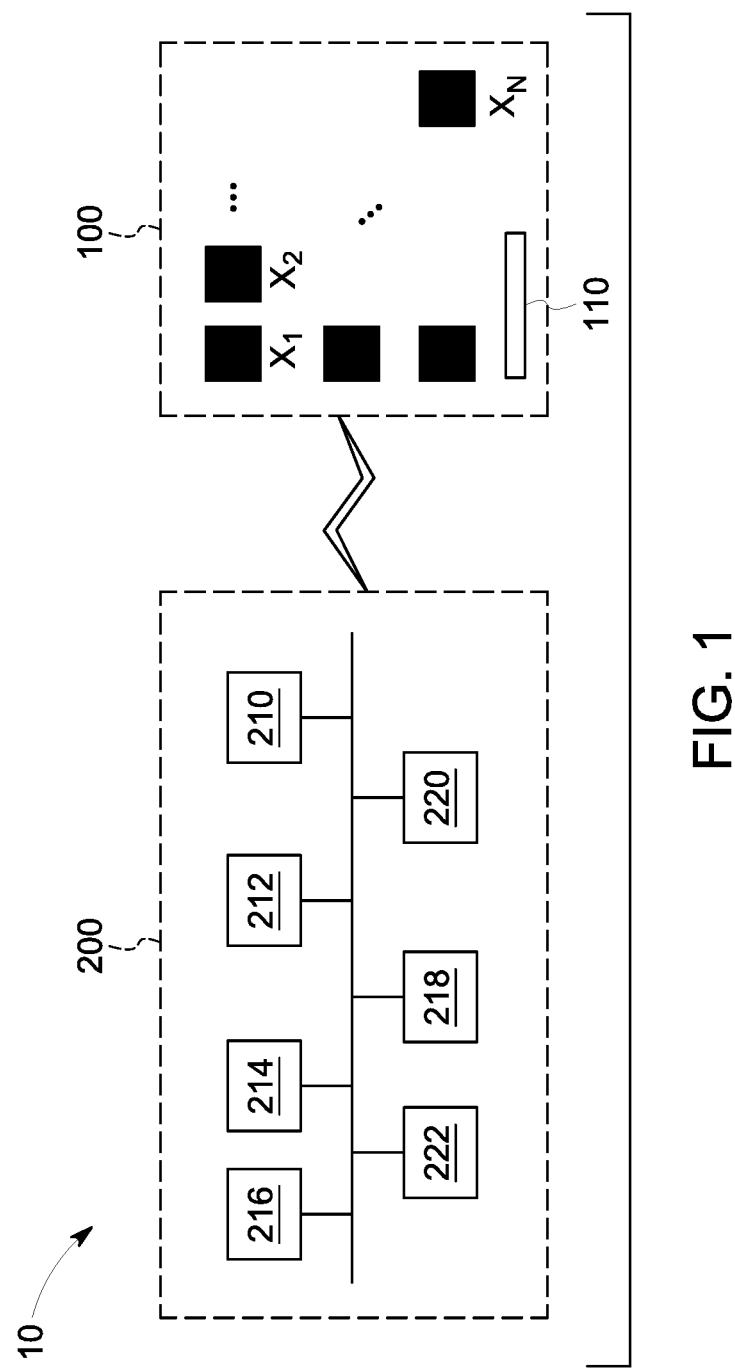
FIG. 1 is a block diagram of an apparatus having a sensor array and a signal processing circuit and configured to output a heart rate.

An exemplary apparatus 10 for non-contact heart rate monitoring is shown in FIG. 1. Apparatus 10 can include an array of sensors 100 and a signal processing circuit 200. Array of sensors 100 in one embodiment can include a plurality of sensors $X_1$-$X_N$ arranged in a pattern. Array of sensors 100 can include one or more reference electrode 110. In one embodiment, there can be associated one or more reference electrode 110 to array of sensors 100. In one embodiment there can be one reference electrode 110 that is shared by each sensor $X_1$-$X_N$ of array of sensors 100. In one embodiment there can be a plurality of reference electrodes 110 each shared by one or more sensor $X_1$-$X_N$ of array of sensors 100. In one embodiment there can be one reference electrode 110 associated to each sensor $X_1$-$X_N$ of array of sensors 100.

One or more reference electrode 110 can establish a reference voltage with respect to the patient either through direct contact or capacitive coupling and may have potentials asserted on it to provide noise reduction and increase effective coupling. In one embodiment one or more reference electrode 110 may be at ground to establish a voltage reference. In one embodiment one or more reference electrode 110 may be actively driven. FIG. 1 shows array of sensors 100 having sensors $X_1$-$X_N$ that may be arranged in any appropriate pattern to cover the area where the patient may be placed and to provide possible redundant coverage over the patient. One or more reference electrode 110 (or an array of reference electrodes) can be placed proximate the sensors $X_1$-$X_N$ of array of sensors 100. In one embodiment array of sensors 100 can include two or more sensors and in one embodiment can include 16 sensors arranged in an M×M pattern e.g. a 4×4 pattern, although array of sensors 100 can include any number of sensors arranged in any pattern. In one embodiment each sensor $X_1$-$X_N$ can be provided by an electrode coupled to a high impedance amplifier.

In one embodiment, signal processing circuit 200 can be processor based. In one embodiment, signal processing circuit 200 can include one or more input/output interface device 210 for communication with, e.g., array of sensors 100, and/or one or more external processing circuit. One or more input/output interface device 210 can include associated analog to digital and or digital to analog circuitry for facilitating bi-directional signal communication with array of sensors 100. Signal processing circuit 200 can also include one or more central processing unit (CPU) 212, one or more memory device 214 (e.g. a random access memory (RAM) and/or cache memory) one or more storage device 216 and one or more output device 220. One or more memory device 214 and/or one or more storage device 216 can define a tangible computer readable storage medium of signal processing circuit 200. Signal processing circuit 200 can include a power supply 222 which can be battery based power supply to facilitate mobile operation of signal processing circuit 200. One or more output device 220 in one embodiment can be provided, e.g., by one or more display with or without an associated touch screen and/or one or more audio output device, e.g. a speaker. Devices 210, 212, 214, 216, 220, and 222 in one embodiment are in communication via a system bus 218. Signal processing circuit 200 can output data to an output device 220 of apparatus 10 provided by a bus connected output device as shown in FIG. 1 and/or to an output device 220 of apparatus 10 provided as an output device in communication with signal processing circuit 200 via input/output interface device 210.

Figure 2:
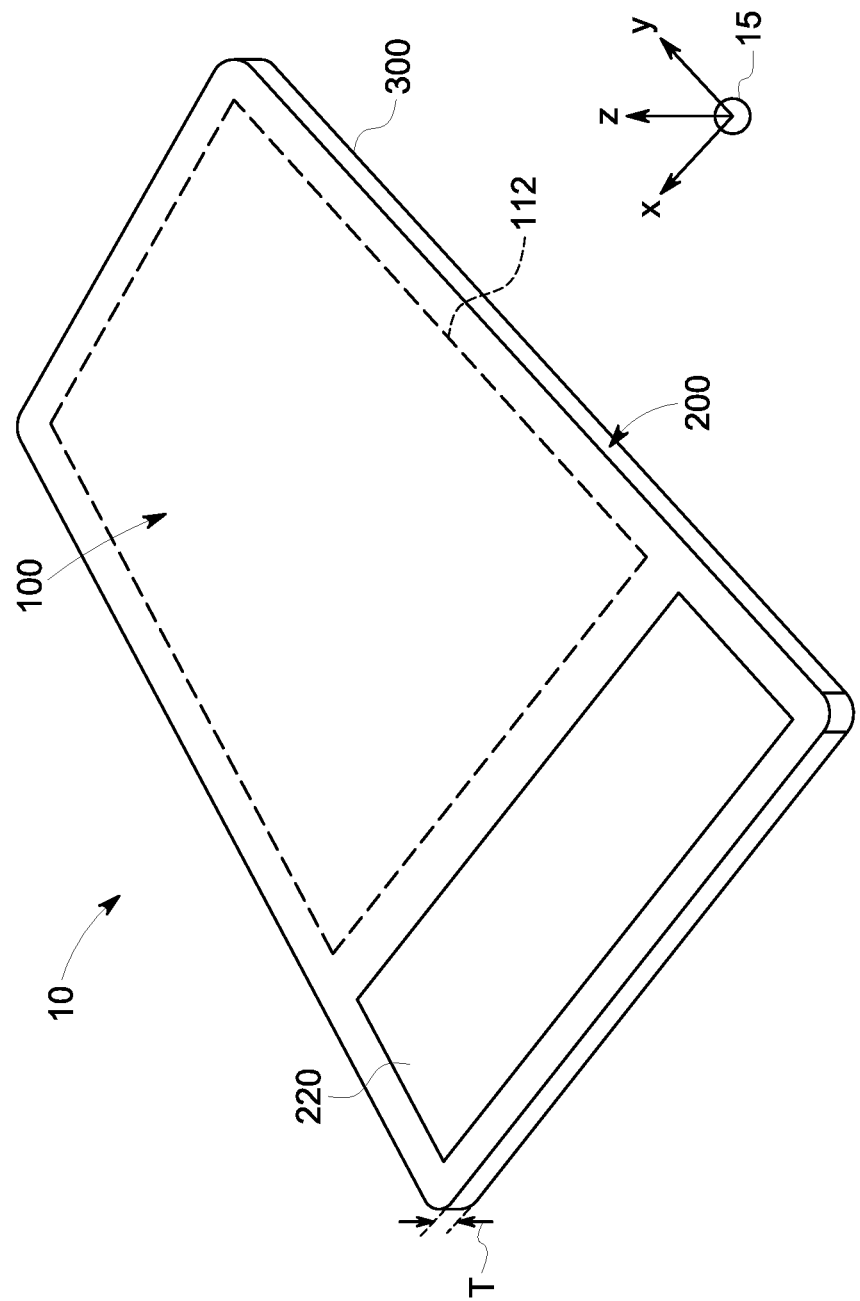
FIG. 2 is a perspective view of a housing that houses an array of sensors and defines a sensor pad.

Referring to FIG. 2, apparatus 10 can include a housing 300 which can be provided e.g. by a low profile housing, e.g. a "pad" profile which can otherwise be termed a "sheet" profile. In the embodiment of FIG. 2, housing 300 can be provided so that apparatus 10 defines a low profile form factor. In one embodiment, housing 300 can house array of sensors 100 to define a sensor pad. In one embodiment, housing 300 can have a substantially uniform thickness, T. In one embodiment, thickness T can be about 5.0 centimeters or less. In one embodiment, thickness T can be about 2.0 centimeters or less. In one embodiment, thickness T can be about 1.0 centimeters or less. In one embodiment, thickness, T, can be about 5.0 mm or less. In one embodiment, thickness T can be about 1.0 mm or less. In one embodiment, housing 300 defining a sensor pad can be flexible and/or conformal to the patient body.

Each sensor $X_1$-$X_N$ of array of sensors 100 in one embodiment can be disc shaped and can include generally planar top surfaces and generally planar bottom surfaces. In one embodiment, each sensor $X_1$-$X_N$ of array of sensors 100 can have a thickness (in a direction parallel to the z axis of reference coordinate system 15) of about 5.0 centimeters or less. In one embodiment, each sensor $X_1$-$X_N$ of array of sensors 100 can have a thickness of about 2.0 centimeters or less. In one embodiment, each sensor $X_1$-$X_N$ of array of sensors 100 can have a thickness of about 1.0 centimeters or less. In one embodiment, each sensor $X_1$-$X_N$ of array of sensors 100 can have a thickness of about 5.0 mm or less. In one embodiment, each sensor $X_1$-$X_N$ of array of sensors 100 can have a thickness of about 1.0 mm or less. According to one embodiment facilitating a low profile each sensor $X_1$-$X_N$ of array of sensors 100 can be arranged so that a top planar surface of the sensor is generally co-planar with each other sensor of the array of sensors 100. In such embodiment each sensor $X_1$-$X_N$ of array of sensors 100 can be regarded to be disposed at a common elevation. Each sensor $X_1$-$X_N$ of array of sensors 100 from a top view (generally in parallel with the z axis of reference coordinate system 15 as shown in FIG. 2) can be equally spaced in the x direction (parallel to the x axis of the reference coordinate system 15) and/or the y direction (parallel to the y axis of the reference coordinate system 15 of FIG. 2), and thus can exhibit a top view (a view in a direction parallel to the z axis of the reference coordinate system 15 of FIG. 2) spatial distribution generally as shown in FIG. 1. Sensors $X_1$-$X_N$ of array of sensors 100 in one embodiment can be spaced apart from one another and can be commonly disposed in a plane parallel to the x-y plane of reference coordinate system 15 (FIG. 2).

Housing 300 can be configured to house components of apparatus 10 as set forth in FIG. 1. For example, in the area within housing 300 indicated generally by dashed border 112 there can be housed array of sensors 100 including sensors $X_1$-$X_N$ and one or more reference electrode 110. Housing 300 can also support output device 220, which in the embodiment of FIG. 2 can be provided by display.

In one embodiment, housing 300 can house one or more component of signal processing circuit 200. Components defining signal processing circuit 200 can be distributed throughout an interior of housing 300. Various materials can be used to provide housing 300, e.g. nylon, acrylic, polyvinyl chloride, polythene, polypropylene, polycarbonate, bakelite, epoxy resin, and/or melamine. Housing 300 can be rigid or flexible. From a top down perspective e.g. looking in a direction parallel with z axis indicated by reference coordinate system 15 (FIG. 2), housing 300 can be rectangular in shape but also can be e.g. circular, oval, or an arbitrary shape.

In the embodiment depicted in FIG. 2, signal processing circuit 200 can be entirely distributed within housing 300. However, in another embodiment signal processing circuit 200 of apparatus 10 can be distributed entirely externally relative to housing 300. In another embodiment, signal processing circuit 200 can be distributed partially internally to housing 300 and partially externally to housing 300. Housing 300 defining a sensor pad can be adapted to be portable. Housing 300 defining a sensor pad can be e.g. disposed as part of patient bedding in a patient care environment during use. Housing 300 defining a sensor pad can be e.g. supported on a person holding a patient (e.g. a mother holding a neonate) in a patient care environment during use. Housing 300 defining a sensor pad can be portable and can be moved between locations in a patient care environment during use.

In one embodiment housing 300 can feature a low profile to facilitate easy insertion under mattress covers or blankets and can be flexible to better conform to the patient. Housing 300 can house signal processing circuit 200 which can include processing and power electronics with a link to external devices that are external to housing 300. The link may be wireless or wired and can serve to communicate control, data, and/or power. Output device 220 which can be provided by a display may display results data. One or more output device 220 can be provided by a display and can be supported by housing 300 and/or can be provided external to housing 300.

Figure 3:
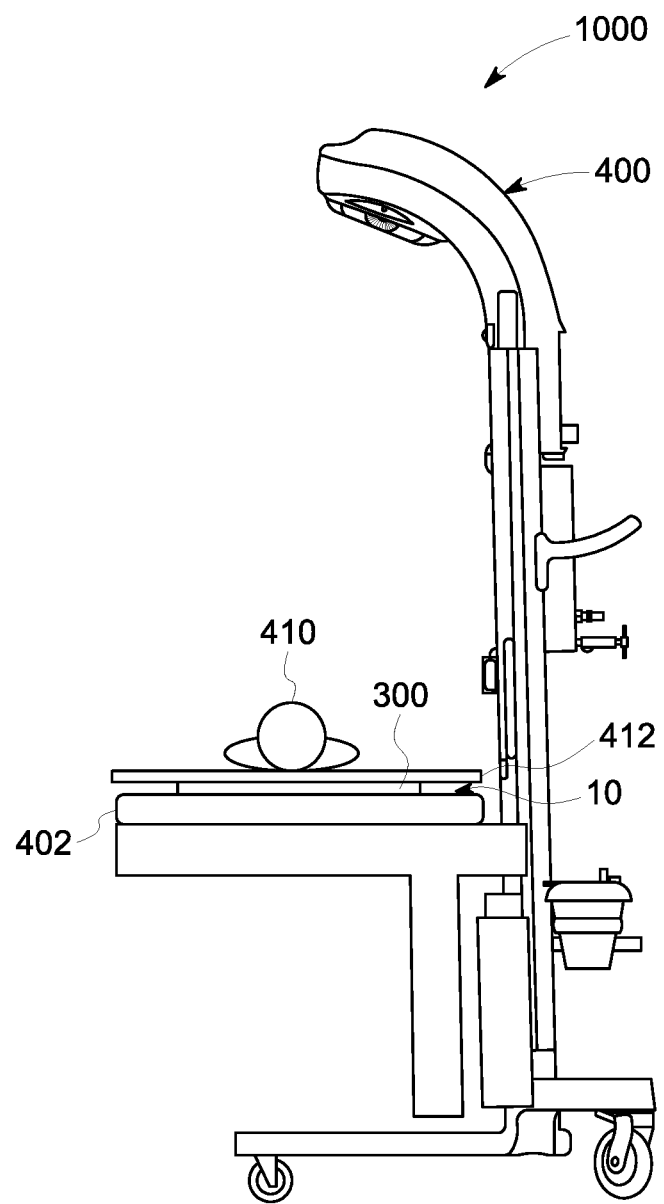
FIG. 3 is perspective view illustrating an application environment incorporating an apparatus having a sensor pad.

FIG. 3 illustrates an example environment of apparatus 10. In the illustrative application depicted in FIG. 3, apparatus 10 can be used in a neonatal care environment 1000. As shown in FIG. 3, environment 1000 can include a neonate radiant warmer 400, which can be referred to as a baby warmer that can include a mattress 402 for supporting a patient 410 provided by a neonate. As shown in FIG. 3, housing 300 defining a sensor pad can be disposed on mattress 402 so that mattress 402 supports the defined sensor pad. One or more blanket 412 can be disposed over housing 300 and patient 410 can be placed on one or more blanket 412. In one use case housing 300 can be portable and moveable between various positions e.g. between a first position supported on mattress 402 and under blanket 412 and a second position supported by a mother's abdomen. For increased portability components disposed within housing 310 e.g. that define an entirety or a part of signal processing circuit 200 can be battery powered via a power supply 222 provided by a battery power supply.

Apparatus 10 can provide heart rate monitoring of patients such as neonates. Apparatus 10 can consist of multiple sensors defining an array of sensors 100 disposed within housing 300 to define a transportable pad that may be inserted under a patient such as a neonate and upon any surface, such as a blanket or mattress or mother's chest or abdomen. Apparatus 10 can feature electronics for non-contact measurement of heart rate, signal conditioning and processing, and display on housing 300 defining a sensor pad and/or on a display external to housing 300 which housing may be flexible and conformal. Apparatus 10 can feature rapid measurement of heart rate even in the case there is movement of the patient such as a neonate and is tolerant of position of the neonate with respect to the array of sensors 100. Array of sensors 100 in one embodiment can be of such size and can include a sufficient number of sensors as to accommodate a range of sizes of patients from neonates to older babies to adults.

Signals generated using one or more non-contacting sensor of array of sensors 100 can be digitally sampled. Signals generated using multiple non-contacting sensors of array of sensors 100 can be digitally sampled and combined. In one embodiment, signal processing circuit 200 can select the best signals to minimize the effects of patient or caregiver motion. Apparatus 10 can provide a numeric heart rate display as well as a data quality indication and/or a simple visual or audio indication of detected cardiac R-wave beats. Apparatus 10 can provide rapid acquisition and display of results, coupled with application of user-specified configuration data including threshold values and can be used to guide resuscitation protocols.

Apparatus 10 can support measurement through multiple blankets or layer of plastic between array of sensors 100 and patient 410. A sensor pad defined by housing 300 can be flexible to conform to the object upon which it is placed which can include e.g. bedding as set forth herein, a patient or a mother's chest or abdomen in the case the patient is a neonate such as a newly born neonate placed upon its mother. Housing 300 housing an array of sensors 100 and defining a sensor pad can be disposable or reusable, with appropriate cleaning and sterilization to enable use of apparatus 10 having housing 300 e.g. in a labor and delivery room or an operating room for neonate deliveries, respectively.

Figure 5:
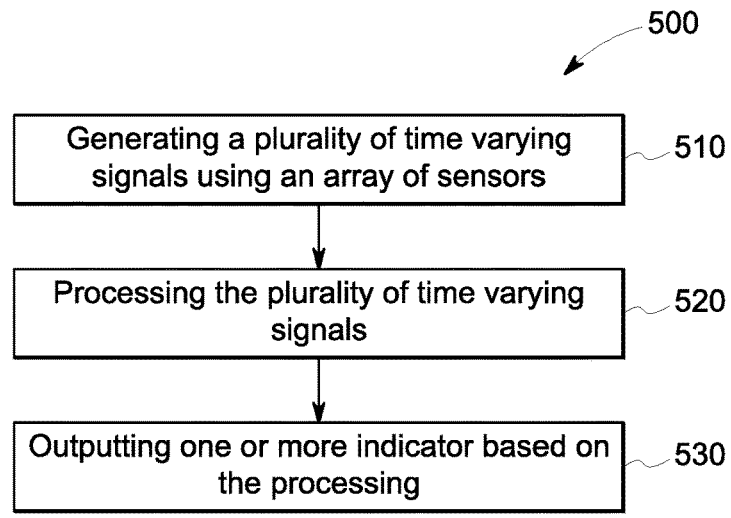
FIG. 5 is flowchart illustrating a method for performance by a signal processing circuit.

Referring to the flowchart of FIG. 5, signal processing circuit 200 of apparatus 10 (FIG. 1), can be configured to perform the method 500, illustrated in reference to the flowchart of FIG. 5. At block 510, signal processing circuit 200 can perform generating a plurality of time varying signals using an array of sensors e.g. array of sensors 100. At block 520, signal processing circuit 200 can perform processing the plurality of time varying signals. At block 530, signal processing circuit 200 can perform outputting one or more indicator based on the processing.

Figure 4:
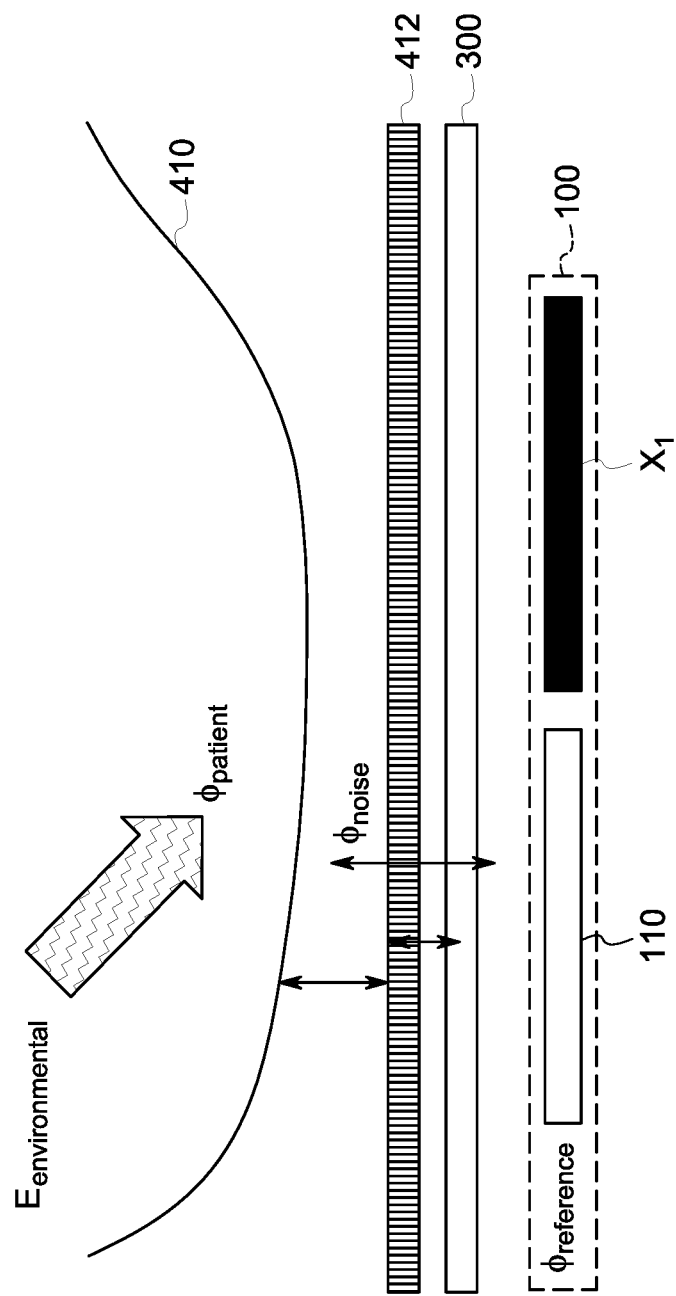
FIG. 4 is schematic diagram illustrating signal dependence of heart motion and contributing noise and interfering signal sources.

Referring to FIG. 4, embodiments herein recognize that a sensor output provided by a voltage at a sensor $X_1$ to $X_N$ of array of sensors 100 in reference to a voltage of one or more reference electrode 110 can provide useful information. Embodiments herein recognize that a voltage of a sensor e.g. $X_1$ of a set of sensors $X_1$ to $X_N$ can be affected by multiple sources of potential in addition to the patient's own body potential including noise potentials deriving from motion, triboelectric effects, and external environmental electrical noise. In reference to FIG. 4, there is shown representative sensor $X_1$, one or more reference electrode 110, housing 300, blanket 412, and patient 410. Embodiments herein recognize that measured voltage at sensor $X_1$ in reference to voltage of one or more reference electrode 110 can be a function of patient potential, $\phi_{patient}$, noise potential, $\phi_{noise}$, and reference potential, $\phi_{reference}$. A sensor voltage, $V_{sensor}$, can be expressed as follows:

$$V_{sensor} = f(\phi_{patient}, \phi_{noise}, \phi_{reference}) \qquad \text{Eq. 1}$$

For performance of method 500, signal processing circuit 200 can process one or more sensor output to develop a plurality of time varying signals. In that more than one sensor output may be indicative of heart rate, the plurality of time varying signals may yield multiple estimates of heart rate (HR) each with an estimated data quality (QHR). Different sensor outputs and/or combinations of sensor outputs may be used to provide reliable measurements at different times as the patient is moved or interacted with and this redundancy provides more consistent overall heart rate measurements. Apparatus 10 can evaluate a plurality of time varying signals to yield a single estimate of heart rate and a confidence value associated to a determined heart rate. Apparatus 10 can clearly e.g. via display and/or audio indication the determined heart rate and/or a determined confidence level associated to a determined heart rate. Time varying signals provided by signal processing circuit 200 can be provided using single sensor outputs over time or combinations of sensor outputs over time. Embodiments herein recognize that providing time varying signals based on a combination of sensor outputs can feature an increased signal to noise ratio, e.g. as a result of one or more of increased signal or noise cancellation. Embodiments herein recognize that spatially separated signal sources e.g. spaced apart first and second sensors of array of sensors 100 can produce equal and opposite signals representing a common heart motion event. Thus, subtracting such signals can result in a signal of increased signal strength. In the case spaced apart first and second sensors share a common charge distribution, subtracting signals from the sources can result in a signal of reduced noise resulting from noise cancellation.

Referring to block 510, signal processing circuit 200 can perform generating a plurality of time varying signals using array of sensors 100. In one embodiment, each time varying signal of the plurality of time varying signals can be provided by a function of one or more sensor output. In one embodiment, each time varying signal of the plurality of time varying signals can be provided by a function of two or more sensor outputs. In one embodiment, as set forth in reference to Eq. 2-4, each time varying signal of the plurality of time varying signals can be provided by a function of two sensor outputs and more particularly can be provided by a difference signal between first and second sensor outputs. A sensor output as set forth herein can be a sensor output voltage with respect to a voltage of one or more reference electrode 110. Signal processing circuit 200 can control a voltage of one or more reference electrode 110 for noise reduction of a sensor output.

Where array of sensors 100 is provided by a 16 sensor 4×4 sensor array having sensors $X_1$ to $X_{16}$ performing block 510 signal processing circuit 200 and a plurality of time varying signals $S_1$ to $S_{120}$ can be provided as follows.

$$S_1(t)=V_{X1}(t)-V_{X16}(t) \quad \text{Eq. 2}$$

$$S_2(t)=V_{X2}(t)-V_{X16}(t) \quad \text{Eq. 3}$$

. . .

$$S_{120}(t)=V_{X15}(t)-V_{X16}(t) \quad \text{Eq. 4}$$

In the example described with reference to Eq. 2-4, $V_{Xi}(t)$ represent time varying signals provided sensor outputs as filtered using one or more filtering process e.g. by notch, bandpass, convolution, and/or other filtering. In the described example, difference voltages over time as set forth in reference to Eq. 2-4 between first and second sensor outputs can be provided using array of sensors 100. Embodiments herein recognize that different sensors may experience similar noise terms. Accordingly embodiments herein recognize that forming appropriately weighted linear combinations of sensors can provide a means for reducing common mode noise or augmenting signals. For providing a difference voltage signal processing circuit 200 can iteratively read different combinations of sensor outputs of sensors of array of sensors 100 and can process the outputs to provide a difference value over time. The difference voltages can be provided to represent different potentials at different spatial areas of array of sensors 100 and patient 410.

Figure 6:
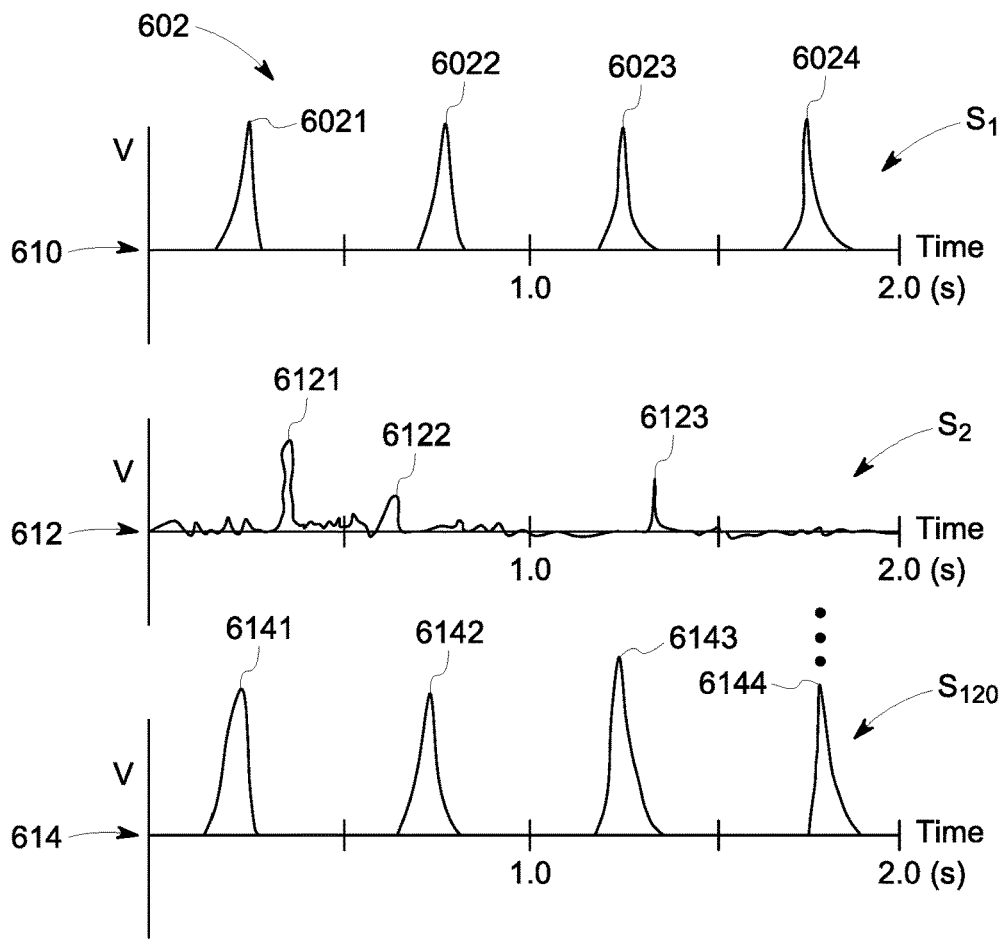
FIG. 6 is a timing diagram illustrating a plurality of time varying signals output using an array of sensors.

Further illustrating features of apparatus 10 is the timing diagram of FIG. 6 having timeline 610 illustrating time varying signal $S_1$, timeline 612 illustrating time varying signals $S_2$, and timeline 614 illustrating time varying signal $S_{120}$. Referring to timing diagram 602, it is illustrated that some signals of the plurality of time varying signals $S_1$ to $S_{120}$ can be representative of a patient's heart motion and other signals can be unrepresentative of a patient's heart motion and may be due to other signal sources including electrical noise or motion artifacts. Referring to timing diagram 602, it is seen that signals $S_1$ and $S_{120}$ can include regular peaks 6021-6024 ($S_1$) and 6141-6144 ($S_{120}$) of consistent interval spacing and therefore can be regarded to be representative of a patient's heart motion. Signal $S_2$ on the other hand, includes irregular peaks 6121-6123 without a consistent interval pattern. Applying rules based processing, signal processing circuit 200 can determine that signal $S_2$ is unrepresentative of the patient's heart motion. Various processes are set forth herein for processing signals $S_1$ to $S_{120}$ to quickly and efficiently discriminate heart motion representative signals from heart motion unrepresentative signals.

In one embodiment signal processing circuit 200 for processing signals $S_1$-$S_{120}$ can score time varying signals $S_1$-$S_{120}$ and can select certain of the signals as heart motion representative signals for use in providing a heart rate based on the scoring. A scoring function in one embodiment can be provided as set forth in Eq. 5.

$$\text{Score}=W_1F_1+W_2F_2+W_3F_3+W_4F_4+W_5F_5+W_6F_6 \quad \text{Eq. 5}$$

Where $F_1$-$F_6$ are factors and $W_1$-$W_6$ are respective weights associated with the various factors. Examples of factors that can be used include: ($F_1$) interval variance; e.g. little variance between intervals between successive peaks can be regarded to be indicative of a heartbeat; ($F_2$) average amplitude of a set of peaks; ($F_3$) peak variance; ($F_4$) standard deviation of the peak intervals; ($F_5$) normalized standard deviation of the intervals normalized by the mean value of the intervals; ($F_6$) absolute peak amplitudes. Signal processing circuit 200 can use fewer factors or a larger number of factors for scoring a plurality of time varying signals $S_1$-$S_{120}$. For providing a score using Eq. 5, signal processing circuit 200 can employ logic operands in addition to or in place of mathematical operands; e.g. a weight of a first factor might be driven to zero or to a certain value on the condition that requirements are satisfied in respect to a second factor. Signal processing circuit 200 can subject the plurality of time varying signals $S_1$-$S_{120}$ to processing via the sliding window processing method described in reference to Table A.

In the example described in reference to Eq. 1-Eq. 5 a plurality of time varying signals can include 120 signals, e.g., signals $S_1$-$S_{120}$. Signal processing circuit 200 can provide a greater number of time varying signals or a smaller number of time varying signals, e.g., can include the plurality of time varying signals $S_1$-$S_K$. In one embodiment, signal processing circuit 200 can provide the plurality of time varying signals $S_1$-$S_{136}$ wherein signals $S_1$-$S_{120}$ are the time varying signals set forth in Eq. 1-Eq. 4 and the signals $S_{121}$-$S_{136}$ are 16 time varying signals providing by sampling over time a sensor output of an individual sensor (e.g. a sensor voltage in reference to a voltage of a reference electrode) of each respective sensor $X_1$ to $X_N$ individually. Signal processing circuit 200 can subject the plurality of time varying signals $S_1$-$S_{136}$ to processing via the sliding window processing method described in reference to Table A. In the described example signal processing circuit 200 can process time varying signals $S_1$-$S_{120}$ provided based on a function of pairs of sensor outputs over time, and time varying signals $S_{121}$-$S_{136}$ can be provided based on individual sensor outputs over time. In another embodiment a subset or an entirety of signals of a plurality of time varying signals $S_1$-$S_K$ can be provided based on functions of three or more sensor outputs over time output by sensors of array of sensors 100.

Signal processing circuit 200 in one embodiment according to the described example based on an output of the scoring function of Eq. 5 can select one or more signal of the plurality of time varying signals $S_1$-$S_K$ for use in determining a heart rate. Signal processing circuit 200 can associate a quality score (QHR) to each signal $S_1$-$S_K$ based on an output of scoring function of Eq. 5. In one embodiment, signal processing circuit 200 can output a heart rate using a single selected signal out of the plurality of time varying signals $S_1$-$S_K$ having the highest score according to the scoring function of Eq. 5. For example signal processing circuit 200 can output a heart rate based on the timing between peaks of a selected signal. In one embodiment, signal processing circuit 200 can output a heart rate using a set of selected signals out of the plurality of time varying signals $S_1$-$S_K$ having the highest N scores (N>=2) according to the scoring function of Eq. 5. For example signal processing circuit 200 can output a heart rate based on the average timing between peaks of a selected set of N signal. A quality score (QHR) determined based on scoring function score e.g. using Eq. 5 can be associated to the output heart rate determined based on the plurality of time varying signals $S_1$-$S_K$ and based on the selected N signals. Providing a user with an indication of a quality score (QHR) (e.g. for a displayed waveform and/or a displayed heart rate) can provide advantages. For example, where a quality score drops over time a caregiver user can be prompted to conduct an alternate measurement of heart rate.

Signal processing circuit 200 can be configured so that processing performed by signal processing circuit 200 can be adaptive to changing conditions including changing positions of a patient e.g. a neonate. Embodiments herein recognize that signals of the plurality of time varying signals $S_1$-$S_K$ that best represent motion of a patient's heart can be expected to change with a changing conditions including changing position of a patient. For configuring signal processing circuit 200 for determining heart rate adaptively based on a changing conditions, signal processing circuit 200 can be configured to iteratively provide updated scores according to scoring function of Eq. 5 and accordingly can be further configured to iteratively update based on results of the scoring function to iteratively update the selected one more signal of the plurality of time varying signals $S_1$-$S_K$ used to determine heart rate.

In one embodiment, signal processing circuit 200 can be configured to iteratively perform scoring of signals of the plurality of time varying signals $S_1$-$S_K$ using Eq. 5 and to iteratively perform selecting of one or more signal for use in determining heart rate iteratively on a sliding window basis. Each window of a sliding window can have an associated predetermined sliding window time scale, e.g. can examine a Q second (e.g. 3 second) time segment of a signal in one embodiment. The time segment of each time window can commence Q seconds before a termination time and can terminate at a termination time. Accordingly, signal processing circuit 200 via performing sliding window processing can discard old/outdated signal values such that signal values attributable to a patient being at a prior position prior to commencement of a current time window do not impact a current heart rate determination performed based on processing of a current time window. Signal processing circuit 200 can be configured to perform updating scoring and signal selecting at predetermined intervals e.g. on a once per second basis in one example. Where signal processing circuit 200 commences a current time window prior to termination of a most recent time window, signal processing circuit 200 can be regarded to perform overlapping sliding window processing. Further aspects of sliding window processing that can be performed by signal processing circuit 200 is set forth in reference to the illustrative example of Table A hereinbelow wherein Q=3.

TABLE A

| WINDOW ORDER | TIME PERIOD (s) | SELECTED SIGNAL (HIGHEST SCORING) |
|---|---|---|
| 1 | 0-3 | $S_{16}$ |
| 2 | 1-4 | $S_{16}$ |
| 3 | 2-5 | $S_{82}$ |
| 4 | 3-6 | $S_{111}$ |
| 5 | 4-7 | $S_{111}$ |
| 6 | 5-8 | $S_{111}$ |
| ... | ... | ... |
| 55 | 54-57 | $S_{50}$ |
| 56 | 55-58 | $S_{50}$ |
| ... | ... | ... |
| 126 | 125-127 | $S_{12}$ |
| 127 | 126-128 | $S_{51}$ |
| ... | ... | ... |

Referring to Table A signal processing circuit 200 for each time window can process each signal of the plurality of time varying signals $S_1$-$S_K$ to perform scoring of each signal of the plurality of time varying signals $S_1$-$S_K$ using Eq. 5 and can select the highest scoring signal of the plurality of time varying signals $S_1$-$S_K$ as the signal for use in determining heart rate. According to the processing set forth in Table A the highest scoring signal can be used by signal processing circuit 200 for determining heart rate. According to another embodiment the highest N scoring signals can be used by signal processing circuit 200 for determining heart rate (e.g. using averages of heart rates using the different signals individually). Referring to Table A, the determined highest scoring signals of the plurality signals $S_1$-$S_K$ can change from window to window but need not change from window to window.

Embodiments herein recognize that it can be advantageous to output a determined heart rate within a restricted time period. Neonates in particular are at risk immediately after birth. Signal processing circuit 200 can be configured for rapid output of heart rate. Typical heart rates range between about 20 and about 200 beats per minute (BPM). In various embodiments, signal processing 200 can be configured to output a heart rate based on first and second successive peaks of an output time varying signal, e.g., $S_1$-$S_K$. In the representative example of FIG. 6, heart rate indicating signals are indicated wherein a heart rate has a value of about 120 BPM. In one embodiment, signal processing circuit 200 can be configured to output heart rate within a time period of a second detected peak plus a processing latency time, which can be minimal. In that first and second peaks representative of heart motion can occur within one second or less, signal processing circuit 200 can output a heart rate within one second or less using hardware and/or software featuring reduced latency. Practically, additional processing encompassing additional processing time (encompassing e.g. 2 s or less, or 3 s or less) can be used for increased accuracy and reliability. By examining first and second and third peaks signal processing circuit 200 is able to make determinations e.g. in regard to interval variance with increased accuracy. In one embodiment, signal processing circuit 200 can be configured to provide a heart rate within a time that is dependent on the number of peaks observed. Thus, signal processing circuit 200 in one embodiment can provide heart rate data faster for faster heart rates. In one embodiment, signal processing circuit 200 can be configured to provide heart rate data responsively to observing two peaks, and thus within about 0.6 seconds in the case of a heart rate of about 200 BPM. In one embodiment, signal processing circuit 200 can be configured to provide heart rate data responsively to observing three peaks, and in another embodiment P peaks.

Figure 7:
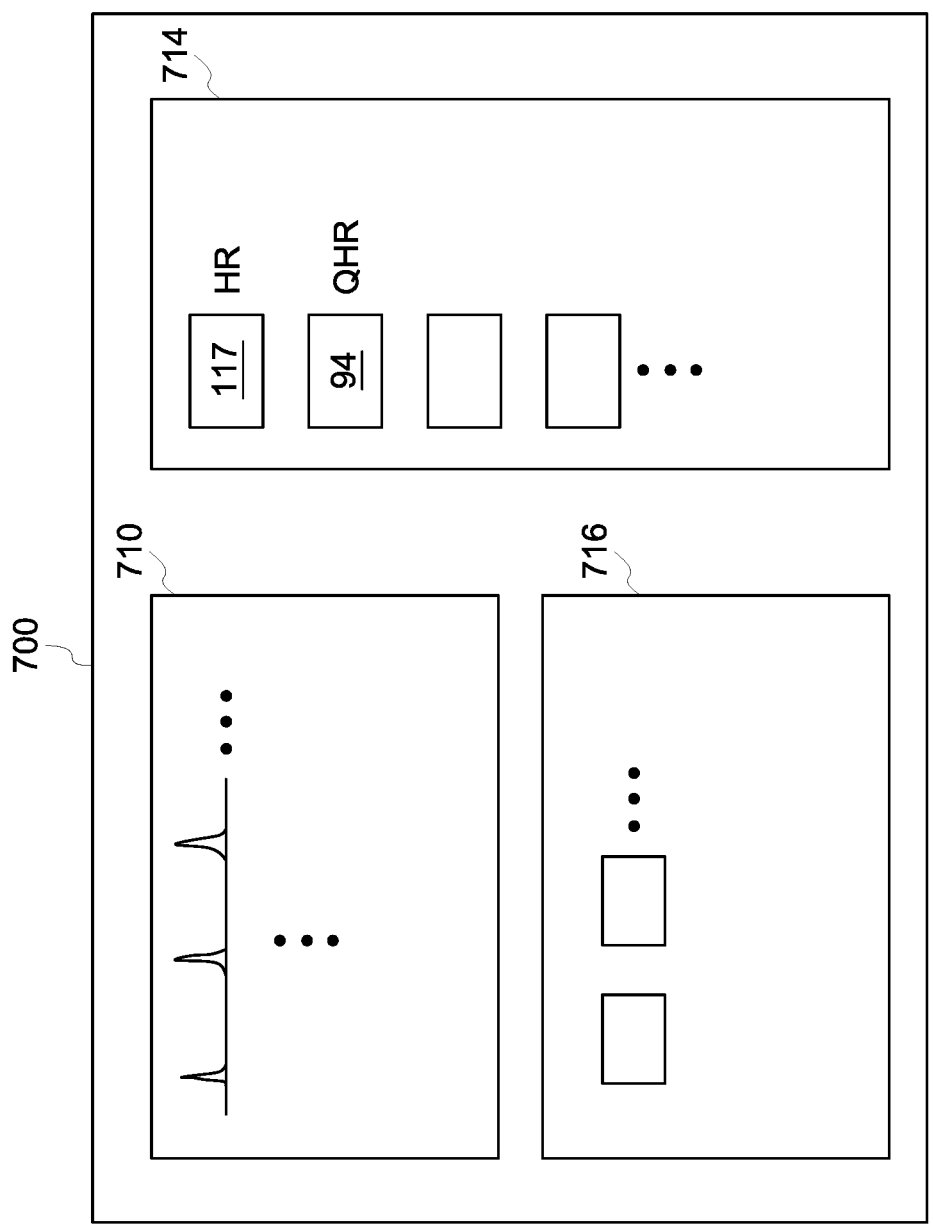
FIG. 7 depicts a user interface for display on an output device provided by a display.

FIG. 7 illustrates an exemplary user interface 700 for display on an output device 220 provided by a display. In area 710 user interface 700 can display one or more waveform. The one or more waveform can represent one or more time varying signal $S_1$-$S_K$ or can represent a combined contribution of a plurality of time varying signals. Area 710 can include control e.g. scrolling functionality that allows a user to scroll between different waveforms representing different signals. In one embodiment, apparatus 10 can be configured so that area 710 by default displays a waveform according to the current highest scoring time varying signal $S_1$-$S_K$ according the current time window processing. Area 710 can include various data visualization features, e.g. can display waveforms representing determined higher scoring and higher quality signals in a different color (e.g. green) than waveforms representing determined lower scoring and lower quality signals (e.g. which can be displayed in red). In area 714 user interface 700 can display e.g. output data such as a current heart rate (HR) of a patient and a quality score (QHR) associated with the current heart rate, and various other data according to configuration data defined by a user. Outputting one or more indicator on a display as set forth herein can include outputting text based data e.g. text based data that specifies a heart rate and/or a level of confidence e.g. as can be indicated by a quality score (QHR). Using area 716 a user can define configuration data. Configuration data defined using area 716 can include e.g. configuration data to define attributes of any aspect of generating, processing, and/or outputting as set forth in reference to method 500 as set forth in reference to FIG. 5. Configuration data defined using area 716 can include e.g. configuration data to specify factors used in a scoring function e.g. as set forth in Eq. 5, weights associated with the various factors. Configuration data defined using area 716 can include e.g. configuration data to define and/or to select for activation neonatal resuscitation guidance processes as set forth herein. Embodiments herein recognize that in different applications different signal attributes can define better indicators of signal quality. Configuration data defined using area 716 can also include e.g. configuration data to define waveform information output in area 710 and other output data output in area 714 or otherwise output visually and/or audibly.

One or more output device 220 can include one or more audio output device e.g. a speaker. Signal processing circuit 200 can be configured to output audio information in addition to or in place of visual information. In one embodiment, signal processing circuit 200 can be configured to output an audio indicator (e.g. one or more beep) responsively to the signal processing circuit 200 providing a heart rate determination. In one embodiment, signal processing circuit 200 can be configured to output an audio indicator (e.g. with a series of beeps) that is a timed to a timing of a sequence of peaks of a time varying signal selected for use in providing a reading of heart rate. In one embodiment, signal processing circuit 200 can be configured to output an audio indicator (e.g. with a siren audio output) to signal an alarm in the case no heart rate or heart rate below a low threshold or above a high threshold is detected. In one embodiment, signal processing circuit 200 can be configured to output an audio indicator (e.g. provided by a voice message) provided to indicate an increasing heart rate condition. In one embodiment, signal processing circuit 200 can be configured to output an audio indicator (e.g. provided by a voice message) provided to indicate a decreasing heart rate condition. The providing of audio information by signal processing circuit 200 can guide various emergency protocols such as neonate resuscitation protocols in the case patient 410 is provided by a neonate.

Features of apparatus 10 in various embodiments make apparatus 10 suitable for use in a variety of applications including emergency applications such as live birth applications in which neonate resuscitation protocols are observed. Housing 300 defining a sensor pad can be portable and can be quickly positioned at a location proximate a current or anticipated location of a patient, e.g. as supported by a mattress. Apparatus 10 can be configured so that array of sensors 100 is in non-contacting relation to a patient when operative to output heart rate data. Accordingly, time consuming set up is not required. Apparatus 10 can process time varying signals representative of patient heart motion responsively to apparatus 10 and a patient being in proximity with one another. Apparatus 10 can be configured so that apparatus 10 provides real time output of indicators determined by processing circuit 200 to a caregiver user and/or patient user. Apparatus 10 can output visual indicators for display and/or audio indicators.

In one embodiment, apparatus 10 can be configured to provide guidance to caregivers for compliance with a neonate resuscitation protocol. For example, the American Heart Association has published a neonatal resuscitation protocol known as the Neonatal Resuscitation Algorithm commonly followed by caregivers. See M. WICKOFF, et al., "2015 American Heart Association Guidelines Update for Cardiopulmonary Resuscitation and Emergency Cardiovascular Care—Part 13: Neonatal Resuscitation," Circulation, AHA Journals, Vol. 132, Issue 18, Nov. 3, 2015. For compliance with a resuscitation protocol a first set of caregiving procedures can be recommended under a first time and heart rate condition (the condition before a certain time threshold and with heart rate under a certain heart rate threshold), a second set of caregiving procedures can be recommended under a second time and heart rate condition (the condition before the certain time threshold and with heart rate above a certain heart rate threshold), a third set of caregiving procedures can be recommended under a third time and heart rate condition (the condition after the certain time threshold and with heart rate under the certain heart rate threshold), and a fourth set of caregiving procedures can be recommended under a fourth time and heart rate condition (the condition after the certain time threshold and with heart rate above the certain heart rate threshold). A set of caregiving procedures herein can include one or more caregiving procedure.

For compliance with a resuscitation protocol provided by the Neonatal Resuscitation Algorithm published by the American Heart Association a first set of caregiving procedures (e.g. PPV, perform $S_pO_2$ monitoring, consider ECG monitoring) can be recommended under a first time and heart rate condition (the condition before a certain time threshold (1 min.) and with heart rate under a certain heart rate threshold (100 BPM)), a second set of caregiving procedures (e.g. position and clear away, supplementary $O_2$ as needed, consider CPAP, postresuscitation) can be recommended under a second time and heart rate condition (the condition before the certain time threshold (1 min.) and with heart rate above the certain heart rate threshold (100 BPM)), a third set of caregiving procedures (e.g. check chest movement, ventilation corrective steps) can be recommended under a third time and heart rate condition (the condition after the certain time threshold (1 min.) and with heart rate under the certain heart rate threshold (100 BPM)), and a fourth set of caregiving procedures (e.g. postresuscitation) be recommended under a fourth time and heart rate condition (the condition after the certain time threshold (1 min.) and with heart rate above the certain heart rate threshold (100 BPM)).

For configuring apparatus 10 to provide guidance to caregivers for compliance with a neonate resuscitation protocol, apparatus 10 can be configured to perform monitoring for conditions that are specified by one or more of a current time from live birth or neonate heart rate and can output one or more visual and/or audio indicators based on the monitoring. Apparatus 10 can be configured to run one or more neonate resuscitation protocol guidance process. When running a neonate resuscitation protocol guidance process, apparatus 10 can provide guidance to caregiver users for compliance with a resuscitation protocol. In one embodiment, apparatus 10 based on a selection defined by a user using user interface 700 can be configured to run a selected one resuscitation protocol guidance processes of a set of candidate resuscitation protocol guidance processes that are summarized in Table B.

TABLE B

| Guidance Process | Description of indicators output by signal processing circuit 200 prior to or at or at or about expiration of a 1 minute time threshold time from birth | Description of indicators output by signal processing circuit 200 subsequent to expiration of a 1 minute time threshold time from birth |
|---|---|---|
| GP1 | A current determined heart rate is displayed visually continuously in area 714 of displayed user interface (FIG. 7). At or about the one minute threshold signal processing circuit 200 further outputs an audio indicator provided by the voice message: "THE ONE MINUTE HEART RATE IS [VALUE] BPM". | A current determined heart rate is displayed visually continuously in area 714 of displayed user interface (FIG. 7). |
| GP2 | A current determined heart rate is displayed visually continuously in area 714 of displayed user interface (FIG. 7). Prior to the one minute threshold signal processing circuit 200 based on a determining that the patient has an under threshold heart rate further outputs an audio indicator providing by rapid beeps and an audio indicator provided by the voice message: "THE HEART RATE AT [VALUE] SECONDS IS [VALUE] BPM. FOLLOW THE LOW HEART RATE PRE-ONE MINUTE PROCEDURES." Prior to the one minute threshold signal processing circuit 200 based on a determining that the patient has an above threshold heart rate further outputs an audio indicator provided by the voice message: "THE HEART RATE AT [VALUE] SECONDS IS [VALUE] BPM. FOLLOW THE NORMAL HEART RATE PRE-ONE MINUTE PROCEDURES." At or about the one minute threshold signal processing circuit 200 further outputs an audio indicator provided by the voice message: "THE ONE MINUTE HEART RATE IS [VALUE] BPM". | A current determined heart rate is displayed visually continuously in area 714 of displayed user interface (FIG. 7). Signal processing circuit 200 based on a determining that the patient has an under threshold heart rate further outputs an audio indicator providing by rapid beeps and an audio indicator provided by the voice message: "THE HEART RATE AT [VALUE] SECONDS IS [VALUE] BPM. FOLLOW THE LOW HEART RATE POST-ONE MINUTE PROCEDURES." Signal processing circuit 200 based on a determining that the patient has an above threshold heart rate further outputs an audio indicator providing by rapid beeps and an audio indicator provided by the voice message: "THE HEART RATE AT [VALUE] SECONDS IS [VALUE] BPM. FOLLOW THE NORMAL HEART RATE POST-ONE MINUTE PROCEDURES." |
| GP3 | A current determined heart rate is displayed visually continuously in area 714 of displayed user interface (FIG. 7). Prior to the one minute threshold signal processing circuit 200 based on a determining that the patient has an under threshold heart rate further outputs an audio indicator providing by rapid beeps and an audio indicator provided by the voice message: "THE HEART RATE AT [BELOW THRRESHOLD VALUE] SECONDS IS [VALUE] BPM. FOLLOW THE LOW HEART RATE PRE-ONE MINUTE PROCEDURES. PERFORM PPV, S$_P$O$_2$ MONITORING, AND PERFORM ECG MONITORING" Prior to the one minute threshold signal processing circuit 200 based on a determining that the patient | A current determined heart rate is displayed visually continuously in area 714 of displayed user interface (FIG. 7). Signal processing circuit 200 based on a determining that the patient has an under threshold heart rate further outputs an audio indicator providing by rapid beeps and an audio indicator provided by the voice message: "THE HEART RATE AT [VALUE] SECONDS IS [BELOW THRESHOLD VALUE] BPM. FOLLOW THE LOW HEART RATE POST-ONE MINUTE PROCEDURES. CHECK CHEST MOVEMENT. PERFORM VENTILLATION CORRECTIVE STEPS IF NEEDED. PERFORM ETT OR PLACE LARYNGEAL MASK IF NEEDED" Signal processing circuit 200 based on a determining that the patient has |

TABLE B-continued

| Guidance Process | Description of indicators output by signal processing circuit 200 prior to or at or at or about expiration of a 1 minute time threshold time from birth | Description of indicators output by signal processing circuit 200 subsequent to expiration of a 1 minute time threshold time from birth |
|---|---|---|
| | has an above threshold heart rate further outputs an audio indicator provided by the voice message: "THE HEART RATE AT [VALUE] SECONDS IS [ABOVE THRESHOLD VALUE] BPM. FOLLOW THE NORMAL HEART RATE PRE-ONE MINUTE PROCEDURES. POSITION AND CLEAR AWAY, PERFORM $S_pO_2$ MONITORING, PERFORM SUPPLEMENTARY O2 AS NEEDED, CONSIDER CPAP". At or about the one minute threshold signal processing circuit 200 further outputs an audio indicator provided by the voice message: "THE ONE MINUTE HEART RATE IS [VALUE] BPM". | an above threshold heart rate further outputs an audio indicator providing by rapid beeps and an audio indicator provided by the voice message: "THE HEART RATE AT [VALUE] SECONDS IS [ABOVE THRESHOLD VALUE] BPM. FOLLOW THE NORMAL HEART RATE POST-ONE MINUTE PROCEDURES. PERFORM POSTRESUSCITATION CARE." |

In the example described in reference to Table B, the resuscitation protocol guidance processes GP1, GP2, and GP3 that can be selected to be run by signal processing circuit 200 based on user defined configuration data can provide different levels of guidance to one or more caregiver user for compliance with a resuscitation protocol provided by the Neonatal Resuscitation Algorithm published by the American Heart Association. With the process GP1 running a caregiver user is given a relatively minor amount of guidance. In an aspect with process GP1 running signal processing circuit 200 can output an audio indicator to indicate heart rate at the threshold time of 1 minute at which time recommendations under both low and normal heart rate conditions according to the protocol change. With the process GP2 running a caregiver user is given a moderate amount of guidance. In an aspect with process G2 running signal processing circuit 200 can output an audio indicator to indicate heart rate at the threshold time of 1 minute at which time recommendations under both low and normal heart rate conditions under the protocol change. In an aspect with process GP2 running signal processing circuit 200 can output audio indicators to provide general reminders as to caregiver procedures to perform under different determined time and patient heart rate conditions ("FOLLOW THE LOW HEART RATE PRE-1 MINUTE PROCEDURES," "FOLLOW THE LOW HEART RATE POST-1 MINUTE PROCEDURES," "FOLLOW THE NORMAL HEART RATE PRE-1 MINUTE PROCEDURES" "FOLLOW THE NORMAL HEART RATE POST-1 MINUTE PROCEDURES"). With the process GP3 running a caregiver user is given an increased amount of guidance. In an aspect with process G3 running signal processing circuit 200 can output an audio indicator to indicate heart rate at the threshold time of 1 minute at which time recommendations under both low and normal heart rate conditions under the protocol change. In an aspect with process GP3 running signal processing circuit 200 can output audio indicators to provide specific reminders as to caregiver procedures to perform under different determined time and patient heart rate conditions ("FOLLOW THE LOW HEART RATE PRE-ONE MINUTE PROCEDURES. PERFORM PPV, $S_pO_2$ MONITORING, AND PERFORM ECG MONITORING," "FOLLOW THE NORMAL HEART RATE PRE-ONE MINUTE PROCEDURES. POSITION AND CLEAR AWAY, PERFORM $S_pO_2$ MONITORING, PERFORM SUPPLEMENTARY O2 AS NEEDED, CONSIDER CPAP," "FOLLOW THE LOW HEART RATE POST-ONE MINUTE PROCEDURES. CHECK CHEST MOVEMENT. PERFORM VENTILATION CORRECTIVE STEPS IF NEEDED. PERFORM ETT OR PLACE LARYNGEAL MASK IF NEEDED," "FOLLOW THE NORMAL HEART RATE POST-ONE MINUTE PROCEDURES. PERFORM POSTRESUSCITATION CARE").

Apparatus 10 can be configured to initiate tracking of a time from a time of live birth according to various processes. In one example, user interface 700 e.g. in area 716 can include an initiate button which when actuated by a caregiver user in response to the caregiver user's observation of live birth initiates time tracking. In one example, apparatus 10 can be configured to initiate tracking of time from a live birth automatically. For example, housing 300 defining a sensor pad can be disposed at a location so that a newly born neonate can be placed in proximity thereto immediately on the occurrence of live birth. With such arrangement apparatus 10 can be configured to automatically initiate time tracking based on initial time varying signals having heart motion representing peaks e.g. as in time varying signal $S_1$ and $S_{120}$ (FIG. 6) being detected by signal processing circuit 200.

In one embodiment, signal processing circuit 200 can be pre-loaded with any number of neonate resuscitation protocol guidance processes e.g. neonate resuscitation protocol guidance processes GP1, GP2, GP3. In one embodiment, apparatus 10 can include e.g. a menu driven development toolkit that allows users to custom configure apparatus 10 to include neonate resuscitation protocol guidance processes in accordance with processes GP1, GP2, GP3 using user defined configuration data entered using area 716 of user interface 700 (FIG. 7). Users can define a greater number of custom configured neonate resuscitation protocol guidance processes or a fewer number of neonate resuscitation protocol guidance processes. Users can also define configuration data using e.g. area 716 of user interface 700 to add or subtract features including any outputting features to any defined neonate resuscitation protocol guidance process including guidance process GP1, GP2, or GP3 or other defined guidance processes. Apparatus 10 can be configured so that any guidance process of apparatus 10 can be customized for increased compatibility with a particular user work flow, e.g. a resuscitation protocol. That protocol might include e.g. visual/and or audio outputting of critical values for display e.g. in area 714 of user interface 700 via a text based readout for display at certain times and/or via a voice message for audio output. That protocol might also include visual and/or audio alarm indicators if values are outside of critical ranges. According to one example, apparatus 10 for configuration in support of a certain protocol can initiate visual and/or audio outputting of heart rate when it is first determined and its time, and/or can initiate outputting at a user defined time e.g. one minute after an initial heart rate determination by signal processing circuit 200. Apparatus 10 based on user defined configuration data defined using area 716 and based on preferences of a particular one or more caregiver user can be configured to perform outputting of indicators automatically e.g. based on monitored timing and/or heart rate conditions, manually, in response to user defined selections made using area 716 during performing of method 500 by signal processing circuit, and/or in part automatically and in part manually. Apparatus 10 in one embodiment can visually and/or audibly output e.g. indicators specifying a master clock, indicators specifying critical events and their values and times, and/or other indicators which indicators can be user configured.

With candidate neonate resuscitation protocol guidance processes developed a user can activate a select one guidance process using area 716. In one embodiment a user can select one of guidance processes GP1, GP2, GP3 based on an experience level of caregiver users providing care in accordance with a neonate resuscitation protocol. The guidance process GP1 (minor guidance) might be selected where the caregiver users are highly experienced. Guidance process GP2 (moderate guidance) might be selected where the caregiver users are moderately experienced. Guidance process GP3 (increased guidance) might be selected where the caregiver users include relatively less experienced caregivers (e.g. trainees). In one embodiment, each guidance process GP1, GP2, and GP3 can be implemented with use of one or more program stored on a computer readable storage medium of signal processing circuit 200 as set forth herein. In one embodiment, apparatus 10 can include a computer program product defined by a computer readable storage medium readable by a processing circuit that stores computer readable program instructions for execution by a processor to perform the functions set forth herein including the functions of method 500 (FIG. 5) and the functions of processes GP1, GP2, and GP3.

Figure 8:
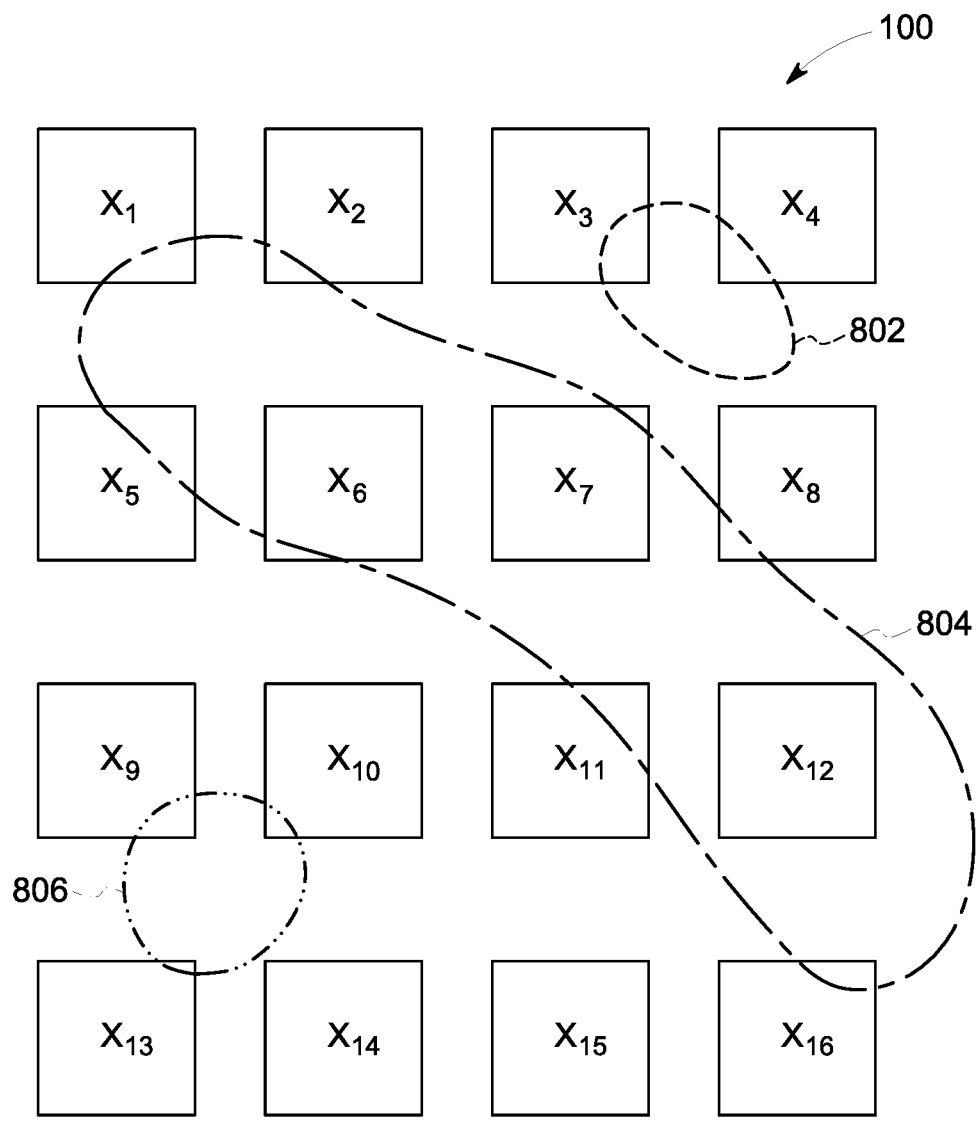
FIG. 8 is a schematic diagram illustrating charge distributions on intervening surfaces between the sensor and patient capable of yielding noise signals due to motion.

Embodiments herein recognize that variety of factors can render certain signals of a plurality of time varying signals $S_1$ to $S_{120}$ unrepresentative of heart motion. Without being bound to any particular theory one possible factor is illustrated in reference to FIG. 8. In one example, array of sensors 100 can be susceptible to charge distributions wherein clusters of charges are distributed in unpredictable patterns over array of sensors 100. Referring to FIG. 8, for example, array of sensors 100 during one possible time period can include charge distribution 802, spread over sensors $X_3$ and $X_4$, charge distribution 804 spread over sensors $X_1$, $X_2$, $X_5$, $X_6$, $X_7$, $X_8$, $X_{11}$, $X_{12}$, and $X_{16}$, and charge distribution 806 spread over sensors $X_9$, $X_{10}$, and $X_{13}$. In the described example, sensors that are tied to the same charge distribution, e.g. $X_6$ and $X_7$ can be expected to provided differential signals (e.g. the difference between a voltage reference signal at sensor signal $X_7$ and the voltage reference signal at sensor signal $X_6$) would be unrepresentative of a patient's heart motion. In one possible scenario where an insulating layer (plastic for example) is placed between array of sensors 100 and patient 410 charge may be present or generated by triboelectric or other mechanisms on the insulating layer. As this layer moves, possibly from patient or physician interaction with the patient, the moving charge can create a spatially varying noise term over the array of sensors 100. Areas with comparable charge and motion may see similar noise artifacts. Accordingly, providing time varying signals for processing based on combinations of sensor outputs can help with noise rejection. Without being bound to a particular theory embodiments herein recognize that sections with fixed charge distributions, like charge distribution 802, charge distribution 804, and charge distribution 806 can have common noise terms and that forming differential pairs within that charge distribution can facilitate noise cancellation to reduce/eliminate the noise term.

Signal processing circuit 200 can include various features for improving quality of time varying signals provided using signal processing circuit 200. In one embodiment, signal processing circuit 200 can include processing features that define a Driven Right Leg (DRL) circuit. A DRL circuit can reduce Common-mode interference. Embodiment herein recognize that a patient's body can act as an antenna which picks up electromagnetic interference, e.g. from electrical power lines. A DRL circuit defined by signal processing circuit 200 can be used to reduce/eliminate interference noise by actively canceling the interference. A DRL circuit defined by signal processing circuit 200 can perform examining of sensor outputs of sensors $X_1$-$X_N$ and based on the examining can drive a voltage of one or more reference electrode 110 for reduction of interference and for improved signal to noise ratio of sensor outputs.

For improved signal to noise ratio of sensor outputs of array of sensors 100 a DRL circuit defined by signal processing circuit 200 can drive one or more reference electrode 110 associated to array of sensors 100 to a Circuit Common voltage. Referring to FIG. 3 embodiments herein recognize that one or more reference electrode 110 of array of sensors 100 can be coupled to patient 410 by an unknown time varying impedance. If the voltage of patient 410 drifts away from a Circuit Common voltage it can be advantageous to return the voltage of patient 410 to Circuit Common as fast as possible. Signal processing circuit 200 can be configured so that based on a positive floating voltage at patient 410 signal processing circuit 200 can drive voltage at one or more reference electrode 110 to negative to remove the positive charge at patient 410. Signal processing circuit 200 can be configured so that based on a negative voltage at patient 410 signal processing circuit 200 can drive voltage at one or more reference electrode 110 to a positive voltage to remove the negative charge at patient 410. Signal processing circuit 200 can be configured to iteratively examine sensor outputs of sensors $X_1$-$X_N$ in order to iteratively estimate a potential at patient 410 and based on the estimate can adjust a drive voltage applied to one or more reference electrode 110 to encourage return of a potential at patient 410 to a Circuit Common voltage.

This written description uses examples to disclose the invention, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Forms of term "based on" herein encompass relationships where an element is partially based on as well as relationships where an element is entirely based on. Forms of the term "defined" encompass relationships where an element is partially defined as well as relationships where an element is entirely defined. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Also, while some embodiments are described as having a certain number of elements it will be understood that the invention can be practiced with less than or greater than the certain number of elements. Accordingly, the invention is not to be seen as limited by the foregoing description, but is only limited by the scope of the appended claims.

The invention claimed is:

1. An apparatus comprising:
   a non-contacting array of sensors adapted for positioning at a position spaced from and proximate a position of a patient; and
   a signal processing circuit in communication with the array of sensors, the signal processing circuit including computer readable instructions stored in a computer readable storage medium for implementation of a plurality of candidate neonatal resuscitation protocol guidance processes, wherein the signal processing circuit is configured for:
   generating a plurality of time varying signals using the array of sensors;
   scoring at least one of the plurality of time varying signals;
   selecting, based on the scoring, one or more signal of the plurality of time varying signals for use in determining a heart rate of the patient;
   determining the heart rate based on the selected one or more signal;
   running a selected guidance process of the plurality of candidate neonatal resuscitation protocol guidance processes to guide a caregiver user in performance of the selected guidance process; and
   outputting one or more indicator based on the determined heart rate and the selected guidance process.

2. The apparatus of claim 1, wherein a time varying signal of the plurality of time varying signals is provided by a function of one or more sensor output, each of the one or more sensor output being a voltage output of a sensor of the array of sensors in respect to a reference electrode.

3. The apparatus of claim 1, wherein the apparatus includes a housing that houses the array of sensors to define a sensor pad.

4. The apparatus of claim 1, wherein the outputting one or more indicator includes outputting the determined heart rate to a display.

5. The apparatus of claim 1, wherein the outputting one or more indicator includes outputting the determined heart rate and a determined confidence level associated to the determined heart rate, to a display.

6. The apparatus of claim 1, wherein the outputting one or more indicator includes outputting an audible indicator.

7. The apparatus of claim 1, wherein the outputting one or more indicator includes outputting an audible indicator, the audible indicator being based on the determined heart rate.

8. The apparatus of claim 1, wherein the selected guidance process of the plurality of candidate neonatal resuscitation protocol guidance processes is selected based on a selection defined by a user using a user interface.

9. The apparatus of claim 1, wherein, according to the selected guidance process, the apparatus performs outputting of a voice message indicator to indicate the determined heart rate of the patient at a time of or about an expiration time of a time threshold that is specified by the selected guidance process.

10. The apparatus of claim 1, wherein, according to the selected guidance process, the apparatus performs outputting of a first voice message to specify a first caregiver process based on an occurrence of a first condition, the first condition being a condition at which a current time is prior to expiration of a time threshold specified by the selected guidance process, and the determined heart rate of the patient is determined to be below a first heart rate threshold specified by the selected guidance process, and wherein, according to the selected guidance process, the apparatus performs outputting of a second voice message to specify a second caregiver process based on an occurrence of a second condition, the second condition being a condition at which a current time is prior to expiration of the time threshold specified by the selected guidance process, and the determined heart rate of the patient is determined to be above a second heart rate threshold specified by the selected guidance process.

11. The apparatus of claim 1, wherein the outputting one or more indicator includes outputting an audible indicator, the audible indicator being based on the determined heart rate, and wherein the audible indicator is an audible indicator indicating a condition selected from the group consisting of (a) an increasing heart rate and (b) a decreasing heart rate.

12. The apparatus of claim 1, wherein the outputting one or more indicator includes outputting an audible indicator, the audible indicator being based on a determined alarm condition selected from the group consisting of no heartbeat, the determined heart rate being below a low threshold, and the determined heart rate being above a high threshold.

13. The apparatus of claim 1, wherein the apparatus includes a portable flexible housing that houses the array of sensors to define a flexible sensor pad, wherein the outputting includes outputting the determined heart rate and a determined confidence level associated to the determined heart rate, to a display, wherein the outputting includes outputting an audible indicator, the audible indicator being based on the determined heart rate.

14. The apparatus of claim 1, wherein one or more time varying signal of the plurality of time varying signals is provided by a function of two or more sensor outputs over time, each of the two or more sensor outputs being a voltage output of a sensor of the array of sensors in respect to a reference electrode.

15. The apparatus of claim 1, wherein one or more time varying signal of the plurality of time varying signals is provided by a difference signal over time between first and second sensor outputs, each of the first and second sensor outputs being a voltage output of a sensor of the array of sensors in respect to a reference electrode.

16. The apparatus of claim 1, wherein each time varying signal of a first plurality of time varying signals of the plurality of time varying signals is provided by a function of one sensor output, each time varying signal of the first plurality of time varying signals being a voltage output over time of a sensor of the array of sensors in respect to a reference electrode, wherein each time varying signal of a second plurality of time varying signals of the plurality of time varying signals is provided by a function of two or more sensor outputs, each time varying signal of the second plurality of time varying signals being a voltage difference signal over time between first and second sensor outputs in respect to the reference electrode.

17. The apparatus of claim 1, wherein a time varying signal of the plurality of time varying signals is provided by a function of one or more sensor output.

18. The apparatus of claim 1, wherein the scoring the at least one of the plurality of time varying signals includes scoring the at least one of the plurality of time varying signals within a common time window.

19. The apparatus of claim 1, wherein the scoring includes performing scoring of time varying signals of the plurality of time varying signals according to a scoring function, the scoring function being a function of weighted factors.

20. The apparatus of claim 1, wherein the scoring includes performing scoring of time varying signals of the plurality of time varying signals according to a scoring function, the scoring function being a function of weighted factors, wherein the scoring includes selecting a set of one or more of the plurality of time varying signals using the scoring function and using the set of one or more of the plurality of time varying signals for determining the heart rate of the patient.

21. The apparatus of claim 1, wherein the array of sensors is disposed in a flexible housing that defines a flexible sensor pad.

22. The apparatus of claim 1, wherein the array of sensors is disposed in a flexible housing that defines a flexible sensor pad, and wherein the signal processing circuit includes an output device provided by a display, the display supported by the flexible housing that houses the array of sensors to define the flexible sensor pad.

23. The apparatus of claim 1, wherein the signal processing circuit performs the generating, the scoring, and the outputting in a time within 10 seconds or less of the patient and the array of sensors being in proximity of one another.

24. The apparatus of claim 1, wherein the signal processing circuit performs the generating, the scoring, and the outputting in a time within 3 seconds or less of the patient and the array of sensors being in proximity of one another.

25. The apparatus of claim 1, wherein the signal processing circuit iteratively performs the generating, the scoring, and the outputting on a sliding window basis so that the outputting is iteratively updated.

26. The apparatus of claim 1, wherein the signal processing circuit iteratively performs the generating, the scoring, and the outputting so that the scoring is iteratively updated, wherein, for successive iterations of the scoring, the signal processing circuit selects a different set of one or more time varying signal of the plurality of time varying signals for use in determining the heart rate.

27. The apparatus of claim 1, wherein the array of sensors is disposed in a housing that defines a sensor pad, and wherein the signal processing circuit includes an output device provided by a display, the display supported by the housing and wherein the outputting includes displaying one or more of the determined heart rate or a determined confidence score associated to the heart rate.

28. A method comprising:
generating a plurality of time varying signals using a non-contacting array of sensors arranged in non-contacting relation to a patient;
scoring at least one of the plurality of time varying signals;
selecting, based on the scoring, one or more signal of the plurality of time varying signals for use in determining a heart rate of the patient;
determining the heart rate based on the selected one or more signal;
running a guidance process to guide a caregiver user in performance of a neonatal resuscitation protocol; and
outputting one or more indicator based on the determined heart rate and the guidance process.

29. The method of claim 28, wherein one or more time varying signal of the plurality of time varying signals is provided by a function of one or more sensor output, each of the one or more sensor output being a voltage output of a sensor of the array of sensors in respect to a reference electrode.

30. The method of claim 28, wherein one or more time varying signal of the plurality of time varying signals is provided by a function of two or more sensor outputs, each of the two or more sensor outputs being a voltage output of a sensor of the array of sensors in respect to a reference electrode.

31. The method of claim 28, wherein each time varying signal of a first set of time varying signals of the plurality of time varying signals is provided by a function of one sensor output, each time varying signal of the first set of time varying signals being a voltage output over time of a sensor of the array of sensors, wherein each time varying signal of a second set of time varying signals of the plurality of time varying signals is provided by a function of two or more sensor outputs, each time varying signal of the second set of time varying signals being a voltage difference signal over time between first and second sensor outputs.

32. The method of claim 28, wherein the array of sensors is disposed in a flexible housing that houses the array of sensors to define a flexible sensor pad, wherein the outputting includes outputting the determined heart rate and a determined confidence level associated to the determined heart rate to a display, and outputting an audible indicator, the audible indicator being based on the determined heart rate.

\* \* \* \* \*